US005892110A

United States Patent [19]
Ramprasad et al.

[11] Patent Number: 5,892,110
[45] Date of Patent: Apr. 6, 1999

[54] HETEROGENEOUS CATALYST FOR THE PRODUCTION OF ACETIC ANHYDRIDE FROM METHYL ACETATE

[75] Inventors: Dorai Ramprasad; Francis Joseph Waller, both of Allentown, Pa.

[73] Assignee: Air Products and Chemicals, Inc., Allentown, Pa.

[21] Appl. No.: 651,138

[22] Filed: May 21, 1996

[51] Int. Cl.$^6$ .................................................. C07C 51/56
[52] U.S. Cl. ........................................... 562/891; 562/891
[58] Field of Search ............................................... 562/891

[56] References Cited

U.S. PATENT DOCUMENTS

| | | | |
|---|---|---|---|
| 4,328,125 | 5/1982 | Drago et al. | 252/426 |
| 4,544,511 | 10/1985 | Isshiki et al. | 260/549 |
| 5,155,261 | 10/1992 | Marston et al. | 562/519 |
| 5,360,929 | 11/1994 | Watson et al. | 562/891 |
| 5,364,963 | 11/1994 | Minami et al. | 562/519 |
| 5,466,874 | 11/1995 | Scates et al. | 562/519 |

*Primary Examiner*—Jose' G. Dees
*Assistant Examiner*—Barbara Badio
*Attorney, Agent, or Firm*—Keith D. Gourley

[57] ABSTRACT

This invention relates to a process for producing acetic anhydride by the reaction of methyl acetate, carbon monoxide, and hydrogen at elevated temperatures and pressures in the presence of an alkyl halide and a heterogeneous, bifunctional catalyst that contains an insoluble polymer having pendant quaternized phosphine groups, some of which phosphine groups are ionically bonded to anionic Group VIII metal complexes, the remainder of the phosphine groups being bonded to iodide. In contrast to prior art processes, no accelerator (promoter) is necessary to achieve the catalytic reaction and the products are easily separated from the catalyst by filtration. The catalyst can be recycled for consecutive runs without loss in activity. Bifunctional catalysts for use in carbonylating dimethyl ether are also provided.

18 Claims, No Drawings

HETEROGENEOUS CATALYST FOR THE PRODUCTION OF ACETIC ANHYDRIDE FROM METHYL ACETATE

This invention was made with Government Support under Contract No. DE-FC22-95PC93052 between Air Products and Chemicals, Inc., and the United States Department of Energy. The Government has certain rights to this invention.

TECHNICAL FIELD OF THE INVENTION

This invention relates to a process for producing acetic anhydride by carbonylating methyl acetate and/or dimethyl ether in the presence of a heterogeneous, bifunctional catalyst. The catalyst contains quaternized phosphine groups, some of which phosphine groups are ionically bonded to anionic Group VIII metal complexes, the remainder being bonded to iodide.

BACKGROUND OF THE INVENTION

Acetic Anhydride ($Ac_2O$) is a chemical that has many uses. For example, it is used in the manufacture of cellulose acetate from cellulose. Acetic anhydride is prepared by the carbonylation of methyl acetate (MeOAc) in the presence of a homogeneous Rh catalyst with a lithium iodide (LiI) promoter. Others have attempted to design heterogeneous catalysts with a view of minimizing the leaching of the metal complex. One such system described in U.S. Pat. No. 4,328,125 is an anion exchange resin to which is ionically bound an anionic metal carbonyl species having the general formula $M_n(CO)_m(X)_p^-$, where M is a transition metal. These catalysts have been described and used for the carbonylation of alcohols for the production of carboxylic acids.

Marston et al. in U.S. Pat. No. 5,155,261 and Minami et al. in U.S. Pat. No. 5,364,963 have described a similar catalyst consisting of a cross-linked 4-vinylpyridine divinylbenzene copolymer containing quaternized pyridine groups supporting a rhodium species. This catalyst is robust and offers higher operating temperature for the carbonylation of methanol to acetic acid. U.S. Pat. No. 5,360,929 discloses the use of these catalysts to produce carboxylic acid anhydrides from carboxylate esters and ethers.

SUMMARY OF THE INVENTION

A process for producing $Ac_2O$ is disclosed wherein methyl acetate (MeOAc) is carbonylated in the presence of a heterogeneous, bifunctional catalyst under conditions sufficient to form Ac2O. The process comprises reacting methyl acetate, hydrogen, carbon monoxide and an alkyl halide in the presence of the bifunctional catalyst. The catalyst comprises an insoluble polymer having pendant quaternized phosphine groups, some of which phosphine groups are ionically bonded to anionic Group VIII metal complexes, the remainder of the phosphine groups being bonded to iodide.

Use of a bifunctional catalyst of the present invention for $Ac_2O$ production has distinct advantages over the use of other catalysts in that accelerators or promoters like LiI are not required and the separation of catalysts from product is made easier. The use of ionic bonding to the Group VIII metal complex also offers a further advantage in that the leaching of metal from the catalyst is minimized. The process is highly selective toward $Ac_2O$, can be completed under short reaction times at high temperatures and pressures, and can proceed efficiently with recycling of the catalyst.

The present invention further provides a heterogeneous, bifunctional catalyst for use in catalyzing the carbonylation of dimethyl ether with acetic acid. The catalyst contains an insoluble polymer having pendant quaternized phosphine groups, some of which phosphine groups are ionically bonded to anionic Group VIII metal complexes, the remainder of the phosphine groups being bonded to iodide.

DETAILED DESCRIPTION OF THE INVENTION

The present invention provides a process for making $Ac_2O$ from MeOAc, carbon monoxide (CO) and hydrogen ($H_2$) in the presence of an alkyl iodide and a bifunctional catalyst that comprises an insoluble polymer having pendant quaternized phosphine groups, some of which phosphine groups are ionically bonded to anionic Group VIII metal complexes, the remainder of the phosphine groups being bonded to iodide, under conditions sufficient to form $Ac_2O$. The formed $Ac_2O$ is then recovered.

The bifunctional catalyst is a heterogeneous catalyst that contains an insoluble polymer having quaternized phosphine groups. The phosphine groups are quaternized by techniques well known in the art using an alkyl halide. Preferred alkyl halides contain from one to six carbon atoms (e.g., lower alkyl). Preferred halides are iodide (I), chloride (Cl) or bromide (Br) and, more preferably iodide. A most preferred alkyl halide is methyl iodide.

The polymer is an organic polymer that is large enough and sufficiently cross-linked to be insoluble in organic solvents and contain pendant phosphine groups that can be quaternized. The phosphine groups can be primary ($RPH_2$), secondary ($R_2PH$) or tertiary ($R_3P$) phosphines where R is an alkyl, cycloalkyl or aryl group having up to 20 carbon atoms. Exemplary phosphine groups are trimethyl phosphine, triethyl phosphine, triisopropyl phosphine, tri-n-butyl phosphine, tri-tert-butyl phosphine, tricyclohexyl phosphine and triphenyl phosphine. A preferred polymer is a copolymer of styrene. More preferably, the polymer is a copolymer of styrene and divinylbenzene.

Following quaternization of the polymer phosphine groups (e.g., refluxing the polymer with an excess of methyl iodide in toluene), the polymer is ionically attached to anionic Group VIII metal complexes. The catalyst of the present invention utilizes a Group VIII metal selected from the group consisting of rhodium (Rh), platinum (Pt), palladium (Pd), iridium (Ir), ruthenium (Ru), cobalt (Co), and nickel (Ni). Preferred Group VIII metals are Rh, Ir and Pd. Rh is most preferred.

The Group VIII metal catalyst used in the catalyst system is present in a catalytically effective amount and such catalytically effective amounts can be readily determined by those of ordinary skill in the art. The amount of Group VIII metal to be incorporated into the catalyst system typically ranges from about 0.01 mol % to about 10 mol % based on the MeOAc present, preferably from 0.03 to about 5 mol %.

In a preferred embodiment, an anionic Group VIII metal complex corresponds to the general formula $[M(CO)_aL_bX_c]$ where M is Rh, Ir or combinations thereof; L is an alkyl or acyl group; X is a halide ion; a is 1, 2, or 3; b is 0 or 1; and c is 2 or 3. The sum of a, b and c is equal to or less than six (i.e., $a+b+c \leq 6$).

In a preferred embodiment, M is Rh, X is Cl, a is $\leq 4$, b is 0, c is 2, the formula of the Group VIII metal complex is $Rh_2(CO)_4Cl_2$, and the anionic species $[Rh(CO)_2I_2]^-$ is incorporated into the polymer.

Using the Rh complexes described above, the maximum Rh content that can be incorporated into the polymer is 20% by weight of the polymer or less. Because the catalyst used in a process of the present invention is bifunctional, it is important that only a portion of the quaternized phosphine groups be ionically bonded to the anionic Group VIII metal complex. By way of example, where the Group VIII metal is Rh, the total content of Rh in the catalyst is less than 20% by weight of the polymer. As shown hereinafter in the Examples, catalysts having between about 2% and 6% by weight of Rh have been successfully used in the preparation of $Ac_2O$.

The quaternized phosphine groups not ionically bonded to the anionic Group VIII metal complex are bonded to iodide ($I^-$). This bonding of I to the catalyst eliminates the need for any extraneous promoter or accelerator in the overall reaction of making $Ac_2O$ from MeOAc.

The term carbonylation, as referred to herein, refers to the reaction of MeOAc, carbon monoxide and hydrogen to form $Ac_2O$ under the enumerated process conditions. Carbonylation can be carried out in a batch mode or a continuous mode over a wide range of temperatures. While the optimum temperature for practicing the present invention will depend upon process stoichiometry, the particular catalyst system utilized, as well as the precise combination of reaction conditions, suitable carbonylation temperatures will range from about 90° C. up to about 225° C. However, the most preferred carbonylation temperatures range from about 150° C. to about 210° C. The carbonylation reaction can be carried out under a wide variety of pressures including pressures ranging from about 100 psig to about 1500 psig. Preferred pressures range from about 500 psig to about 1000 psig. Most preferred reaction conditions are a temperature of 190° C. and a pressure of 800 psig. The products of the reaction are analyzed by gas chromatography at various times during the reaction and also in a batch mode (i.e., at the end of the reaction). The catalyst can be removed by filtration and reused for a new feed without a loss in initial activity.

Carbon monoxide and hydrogen are present in the reaction mixture in a stoichiometric ratio of greater than 92:8. Preferably, that stoichiometric ratio ranges from 92:8 to 99:1. Even more preferably, that stoichiometric ratio is 95:5. The desired product ($Ac_2O$) is recovered from the product mixture using standard procedures well known in the art.

The MeOAc used in a process of the present invention can be provided directly or formed from dimethyl ether (DME) and acetic acid (HOAC) as part of the overall reaction scheme. In the latter embodiment, DME, HOAc, carbon monoxide and hydrogen are reacted in the presence of an alkyl halide and a bifunctional catalyst as set forth above. The reaction conditions used are the same as set forth above.

Reaction time is not critical in practicing the present invention and one of ordinary skill in the art can determine optimum reaction times based upon the enumerated reaction conditions, catalyst system and catalyst concentration presented herein. Reaction times required to produce a desired amount of $Ac_2O$ will also depend upon the reaction temperature and pressure. Typically, reaction times range from 0.5 hours to 4.0 hours.

In contrast to prior art processes, no accelerator is necessary to achieve the catalytic reaction and the products are easily separated from the catalyst by filtration. The catalyst can be recycled without loss in activity.

The following examples are presented to further illustrate the scope of the present invention and are not intended to limit the scope thereof.

EXAMPLE 1

PREPARATION Of BIFUNCTIONAL, PHOSPHINE CATALYST

Lithium wire (0.212 g) was broken into small pieces and placed in a flask containing 10 ml of tetrahydrofuran. Chlorodiphenylphosphine (3.12 g) was added to the wire mixture followed by the addition of another 10 ml of tetrahydrofuran. The mixture was stirred under nitrogen for 24 hours to give a red solution of lithium diphenylphosphide. The solution was filtered and to the filtrate was added 5 g of 2% cross-linked Merrifield's resin, which had been previously dried under vacuum. An additional 25 ml of tetrahydrofuran was added and the mixture stirred for another 24 hours under nitrogen. The phosphinated resin was filtered and washed with 3×50 ml of tetrahydrofuran. The resin was further washed with 2×50 ml of acetone and finally with 50 ml of pentane and then dried under vacuum.

50 ml of toluene was added to approximately 2 g of the phosphinated resin. Following the addition of 10 ml of methyl iodide, the slurry was heated at 100° C. for 24 hours. The phosphonium iodide salt of the resin was filtered, washed with 50 ml of toluene and then dried under vacuum.

The rhodium complex $Rh_2(CO)_4Cl_2$ (0.21 g) was dissolved in 100 ml of toluene and added to the phosphonium iodide salt of the resin from the previous step. After stirring for 24 hours, the resin was brown in color and the toluene was colorless indicating that all the rhodium was in the resin. The resin was filtered and characterized via infrared spectroscopy. Two strong carbonyl bands were observed at 2053, 1981 cm-1 characteristic of the species $[Rh(CO)_2IX]^-$, where X=Cl or I. This finding proves that the rhodium complex was ionically attached to the phosphonium salt of the resin.

EXAMPLE 2

CATALYST EVALUATION AND RECYCLE

The following studies were performed to evaluate a bifunctional catalyst of the present invention. An autoclave was charged with methyl acetate (0.695 mol), methyl iodide (0.074 mol), acetic acid (0.29 mol), and 0.8 g of the catalyst prepared in accordance with the procedures of Example 1. The autoclave was pressurized with a 95/5 mix of $CO/H_2$ and the reaction was run at 750 psig and 190° C. After 4 hours, the liquid samples were analyzed by gas chromatography. The reaction was repeated using the same catalyst, but with a fresh charge of reactants. The results of these studies are summarized in Table 1, below.

For comparison purposes, the effects of a phosphine catalyst of the present invention were compared to another bifunctional catalyst, designated as a Reillex™ catalyst. The Reillex™ catalyst was prepared as follows. A sample of Reillex™ 425 (24 g) was dried in an oven at 100° C. for 14 hours. The dried polymer beads were placed in a flask which contained 125 ml of toluene and the mixture was refluxed for 30 minutes under nitrogen. After cooling to room temperature, 20 ml of methyl iodide was added and the resulting mixture was heated at 95° C. for 48 hours and then stirred at room temperature for another 5 days. The yellow beads/powder was filtered and dried under vacuum for 8 hours. Approximately 0.36 g of the Group VIII metal complex $Rh_2(CO)_4Cl_2$ was dissolved in 100 ml of toluene. About 3.36 g of quaternized Reillex™ prepared in the previous step was added, the mixture was stirred for approximately 24 hours and the powder was filtered. No color was observed in the filtrate indicating that all the rhodium was on the polymer. The Reillex™ material contained about 5.1% by weight of rhodium.

By using this method and by varying the amount of complex, a 2.24% Rh containing polymer was also prepared.

TABLE 1

| Catalyst | MeOAc Conv. % | Ac$_2$O turnover freq, (hr$^{-1}$) |
|---|---|---|
| Phosphine 5.4% Rh | 34 | 122 |
| Recycle | 37 | 141 |
| Reillex 2.24% Rh | 51.0 | 153 |
| Recycle | 46.5 | 117 |
| Reillex 5.1% | 35.8 | 137 |
| Recycle | 33.6 | 120 |
| Homogeneous, no LiI | 30 | 99 |
| Homogeneous, with LiI | 77 | 332 |

The results show that the phosphinated catalyst is slightly better that the Reillex™ material at comparable Rh loading. Also, the heterogeneous phosphine catalyst can be recycled without any apparent loss of activity. In contrast, the Reillex™ catalyst, at both Rh loadings, lost activity when recycled. All the heterogeneous systems are better than the homogeneous catalyst used without the LiI promoter.

What is claimed is:

1. A process for producing acetic anhydride which comprises reacting methyl acetate with carbon monoxide and hydrogen in the presence of an alkyl iodide and a bifunctional catalyst that comprises an insoluble polymer having pendant quaternized phosphine groups, some of which phosphine groups are ionically bonded to anionic Group VIII metal complexes, the remainder of the phosphines being bonded to iodide, under conditions sufficient to form acetic anhydride, recovering the formed acetic anhydride, and recycling the bifunctional catalyst to further react methyl acetate with carbon monoxide and hydrogen according to the process.

2. The process according to claim 1 wherein the methyl acetate is formed from dimethyl ether and acetic acid.

3. The process of claim 1 wherein the Group VIII metal complex contains rhodium and iridium.

4. The process according to claim 3 wherein the Group VIII metal complex contains rhodium.

5. The process according to claim 4 wherein the Group VIII metal complex has the formula $[Rh(CO)_2I_2]^-$.

6. The process of claim 1 wherein the alkyl iodide is methyl iodide.

7. The process according to claim 1 wherein the insoluble polymer is a co-polymer of styrene and divinylbenzene having pendant phosphine groups.

8. The process according to claim 1 wherein the reaction conditions comprise a temperature ranging from 90° C. to about 225° C., a pressure ranging from 100 psig to 1500 psig, and a reaction time of greater than 0.5 hours.

9. The process according to claim 8 wherein the temperature ranges from 150° C. to 210° C. and the pressure ranges from 500 psig to 1000 psig.

10. The process according to claim 9 wherein the temperature is 190° C. and the pressure is 800 psig.

11. The process according to claim 1 wherein carbon monoxide (CO) and hydrogen (H$_2$) are present in a stoichiometric ratio (CO:H$_2$) of from 99:1 to 92:8.

12. The process according to claim 11 wherein the stoichiometric ratio of carbon monoxide to hydrogen is, 95:5.

13. The process according to claim 1 wherein the catalyst is prepared by reacting an insoluble polymer having quaternized phosphine groups with a Group VIII metal complex of the formula $[M(CO)_aL_bX_c]^-$, where M is Rh or Ir, or combinations thereof; L is an alkyl or acyl group; X is a halide ion; a is 1, 2, 3 or 4; b is 0 or 1; and c is 2 or 3, and wherein a+b+c $\leq$6.

14. The process according to claim 13 wherein M is Rh; X is Cl; a is $\leq$4; b is 0 and c is 2.

15. A process for producing acetic anhydride which comprises reacting methyl acetate, carbon monoxide, and hydrogen in the presence of methyl iodide and a bifunctional catalyst comprising an insoluble polymer having quaternized phosphine groups, some of which phosphine groups are ionically bonded to $[Rh(CO)_2I_2]^-$, the remainder of the phosphine groups being bonded to iodide, under conditions sufficient to form acetic anhydride, recovering the formed acetic anhydride, and recycling the bifunctional catalyst to further react methyl acetate with carbon monoxide and hydrogen according to the process.

16. The process according to claim 15 wherein the methyl acetate is formed from dimethyl ether and acetic acid.

17. The process according to claim 15 wherein the reaction conditions comprise a temperature ranging from 90° C. to 225° C. and a pressure ranging from 100 psig to 1500 psig.

18. The process according to claim 17 wherein the temperature is 190° C. and the pressure is 800 psig.

* * * * *